US006984826B2

(12) United States Patent
Miller et al.

(10) Patent No.: US 6,984,826 B2
(45) Date of Patent: Jan. 10, 2006

(54) RADIATION DETECTION APPARATUS

(75) Inventors: Eric Miller, Los Gatos, CA (US); Richard Scott Rader, Menlo Park, CA (US); Timothy N. Wells, Ridgefield, CT (US); Paul Stoppel, Wayland, MA (US)

(73) Assignees: United States Surgical Corporation, Norwalk, CT (US); Radiation Monitoring Devices, Watertown, MA (US)

( * ) Notice: Subject to any disclaimer, the term of this patent is extended or adjusted under 35 U.S.C. 154(b) by 0 days.

(21) Appl. No.: 10/869,145

(22) Filed: Jun. 16, 2004

(65) Prior Publication Data

US 2004/0238748 A1   Dec. 2, 2004

Related U.S. Application Data

(60) Continuation of application No. 10/338,954, filed on Jan. 8, 2003, which is a continuation of application No. 09/810,132, filed on Mar. 16, 2001, now Pat. No. 6,534,770, which is a division of application No. 09/177,636, filed on Oct. 23, 1998, now Pat. No. 6,242,741.

(51) Int. Cl.
    *G01T 1/161*   (2006.01)
(52) U.S. Cl. .............................................. 250/363.02
(58) Field of Classification Search ........... 250/363.02, 250/363.1; 600/436
    See application file for complete search history.

(56) References Cited

U.S. PATENT DOCUMENTS 3,427,454 A    2/1969   Webb

| 3,598,109 A | 8/1971 | Kobayashi et al. |
| 3,665,916 A | 5/1972 | Kobayashi et al. |
| 3,669,095 A | 6/1972 | Kobayashi et al. |
| 3,670,719 A | 6/1972 | Kobayashi et al. |
| 3,863,623 A | 2/1975 | Trueblood et al. |
| 4,015,592 A | 4/1977 | Bradley-Moore |
| 4,092,980 A | 6/1978 | Frank et al. |
| 4,243,884 A | 1/1981 | Avera, Jr. |
| 4,255,659 A | 3/1981 | Kaufman et al. |

(Continued)

FOREIGN PATENT DOCUMENTS

EP        0282832 A1    9/1988

(Continued)

OTHER PUBLICATIONS

Richard D. Baxter, "Miniature Hybrid Preamplifier for CdTe Detectors", pp. 493-497, IEEE Transactions on Nuclear Science, vol. NS-23, No. 1, Feb. 1976.

(Continued)

*Primary Examiner*—Constantine Hannaher

(57)   ABSTRACT

A radiation detection apparatus having a hand-held radiation detection probe with a switch assembly removably mounted thereon is hereinafter disclosed. The switch assembly having first and second switches, one to initiate transmission of electrical signals representing scintillations detected over a set time period to a remotely located control unit for counting and averaging, and the other to direct the control unit to download and preferably record the counted and averaged scintillation values for further use. The switch assembly has an insulating member for electrically insulating the switches from the probe, and spaced gripping members that releasably grip the probe. A movable stand is provided preferably with a holder for holding the probe. The probe can have a protective cover thereon with a switch assembly mounted onto the probe over the cover.

9 Claims, 5 Drawing Sheets

U.S. PATENT DOCUMENTS

| | | | |
|---|---|---|---|
| 4,301,367 A | 11/1981 | Hsu | |
| 4,311,145 A | 1/1982 | Esty et al. | |
| 4,338,521 A | 7/1982 | Shaw et al. | |
| 4,545,375 A | 10/1985 | Cline | |
| 4,649,276 A | 3/1987 | Suzuki | |
| 4,682,604 A | 7/1987 | Fymat et al. | |
| 4,688,569 A | 8/1987 | Rabinowitz | |
| 4,782,840 A | 11/1988 | Martin, Jr. et al. | |
| 4,801,803 A | 1/1989 | Denen et al. | |
| 4,887,615 A | 12/1989 | Taylor | |
| 4,889,991 A | 12/1989 | Ramsey et al. | |
| 4,893,013 A | 1/1990 | Denen et al. | |
| 4,932,412 A | 6/1990 | Goldenberg | |
| 4,959,547 A | 9/1990 | Carroll et al. | |
| 5,008,546 A | 4/1991 | Mazziotta et al. | |
| 5,036,201 A | 7/1991 | Carroll et al. | |
| 5,057,690 A | 10/1991 | Morgan et al. | |
| 5,070,878 A | 12/1991 | Denen | |
| 5,140,040 A | 8/1992 | DeBernardis | |
| 5,148,040 A | 9/1992 | Wise, Jr. et al. | |
| 5,151,598 A | 9/1992 | Denen | |
| 5,158,086 A | 10/1992 | Brown et al. | |
| 5,166,073 A | 11/1992 | Lefkowitz et al. | |
| 5,170,055 A | 12/1992 | Carroll et al. | |
| 5,246,005 A | 9/1993 | Carroll et al. | |
| 5,304,763 A | 4/1994 | Ellmann et al. | |
| 5,428,223 A | 6/1995 | Jatteau et al. | |
| 5,429,133 A | 7/1995 | Thurston et al. | |
| 5,441,050 A | 8/1995 | Thurston et al. | |
| 5,456,260 A | 10/1995 | Kollias et al. | |
| 5,475,219 A | 12/1995 | Olson | |
| 5,495,111 A | 2/1996 | Thurston et al. | |
| 5,635,717 A | 6/1997 | Popescu | |
| 5,682,888 A | 11/1997 | Olson et al. | |
| 5,732,704 A | 3/1998 | Thurston et al. | |
| 6,236,880 B1 * | 5/2001 | Raylman et al. | 600/436 |
| 6,242,741 B1 | 6/2001 | Miller et al. | |
| 6,267,726 B1 | 7/2001 | Grimm | |
| 6,534,770 B2 | 3/2003 | Miller et al. | |
| 6,771,802 B1 * | 8/2004 | Patt et al. | 382/128 |

FOREIGN PATENT DOCUMENTS

| | | |
|---|---|---|
| EP | 0371903 A1 | 6/1990 |
| GB | 2117900 | 10/1983 |
| WO | WO 9703369 A1 * | 1/1997 |
| WO | WO/0025150 A1 | 5/2000 |

OTHER PUBLICATIONS

C.L. Colton and J.G. Hardy, "Evaluation of a Sterilizable Radiation Probe as an Aid to the Surgical Treatment of Osteoid-Osteoma", pp. 1019-1021, J. Bone and Joint Surg., vol. 65-A No. 7, Sep. 1983.

E.P. Szypryt, J.G. Hardy, & C.L. Colton, "An Improved Technique Of Intra-Operative Bone Scanning", pp. 643-646, J. Bone and Joint Surg., vol. 68-B, No. 4, Aug. 1986.

Radiation Monitoring Devices, Inc., "Gamma Guidance System from RMD", 2 pages, (a Product Bulletin Published by RMD Inc., in Oct. 1997).

Radiation Monitoring Devices, Inc., "Nuclear Instruments by RMD", 2 pages, (a Product Bulletin Published by RMD Inc., in 1981). NOTE: the month need not be specified as 1981 is much earlier than the US filing date of Oct. 23, 1998.

Radiation Monitoring Devices, Inc., "Technetium, 14MM Surgical Probe System from RMD", 1 page, (a Product Bulletin Published by RMD Inc., in 1996). NOTE: the month need not be specified as 1996 is much earlier than the US filing date of Oct. 23, 1998.

Rik Pijpers et al., "Sentinel Node Biopsy in Melanoma Patients: Dynamic Lymphoscintigraphy Followed by Intraoperative Gamma Probe and Vital Dye Guidance." pp. 788-792, World J. Surg., Oct. 21, 1997. NOTE: The attached copy (pp. 1-13) is of the original article, submitted to the World J. Surg.

"Build a Personal Radiation Monitor," Popular Electronics, by John Steidley, Martin Nakashian and Gerald Entine, Jan. 1980, pp. 39-46.

"Use of a Cadmium Telluride Detector in a New Tiny Personal Radiation Chirper" by Michael A. Wolf, C. John Umbarger and Gerald Entine, IEEE Transactions on Nuclear Science, vol. NS-26, No. 1, Feb. 1979.

"Radiation Detector Probes for Tumor Localization Using Tumor-Seeking Radioactive Tracers" by J. M. Woolfenden H. B. Barber, American Journal Roentgenology article (153: 35-39) Dept. of Radiology, University of Arizona, Tucson 85724, Jul. 1989.

"Performance Comparison of Surgical Gamma Probes." A. van Lingen, et al, from the Journal of Nuclear Medicine Abstract Book Supplement, vol. 38, pp. 208-209, May 1997.

"New Product Release, Nuclear Surgical Probe" by Radiation Monitoring Devices, Inc., one page, Jan. 1985.

"A Surgical Imaging Probe for Tumor Dection" N. E. Hartsough, et al, From the Journal of Nuclear Medicine, vol. 30, #5, p 891, May 1989.

Cover page of brochure entitled 83rd annual Clinical Congress with handwriting at the bottom, which indicates that the Radiation Monitoring Device, Inc. (RMD) Gamma Guidance System featured in the RMD booth #501 was shown at the 83rd annual Clinical Congress on Oct. 12-17, 1997.

* cited by examiner

RADIATION DETECTION APPARATUS

CROSS-REFERENCE TO RELATED APPLICATIONS

This application is a continuation of U.S. application Ser. No. 10/338,954, filed Jan. 8, 2003, which is a continuation of U.S. application Ser. No. 09/810,132, filed Mar. 16, 2001, now U.S. Pat. No. 6,534,770, which is a divisional of U.S. application Ser. No. 09/177,636, filed Oct. 23, 1998, now U.S. Pat. No. 6,242,741, the disclosures of which are hereby incorporated by reference in their entirety.

BACKGROUND OF THE INVENTION

1. Field of the Invention

The present invention relates to a radiation detection apparatus. More particularly, the present invention relates to an apparatus for detecting, quantizing and mapping radiation emitted from a scintillation fluid having gamma-emitting isotopes. The apparatus is battery operated and has a hand-held probe for detecting radiation, and for transmitting electrical signals that represent the detected radiation to a remote unit to process the signals into information. The hand-held probe is a scintillation detector that has a switch assembly removably mounted on the probe for initiating remotely electrical signals to a control unit.

The switch assembly has preferably two finger-operated triggers. One trigger initiates the count, and the other trigger directs the remote unit to download, and preferably record, the counted scintillations or averaged scintillation values for further use.

2. Description of the Prior Art

Procedures for detecting, quantizing and localizing or mapping carcinomas in living beings are known. A radiation-emitting substance is passed through a patient's body. Either a radiation detector device is secured to the patient's body, or a hand-held probe is held adjacent a series of sites surrounding a suspected tumor. One procedure involves injecting a scintillation fluid containing, for example, technetium 99, in quadrants of the capillary system located about a site to determine whether cancer has spread to the lymphatic system. Since fluid drains from the injected area through the lymphatic system, the scintillation detector allows identification and location of the sentinel node, the first lymph node draining the most scintillation fluid and emitting the highest number of scintillations in the lymphatic drainage path from the tumor.

Heretofore, each radiation detecting, quantizing and mapping apparatus has been connected by hardwire to an electrical receptacle or has a battery that discharges during use. One conventional apparatus has a foot pedal connected to a remote unit to initiate counts. The foot pedal does not activate a downloading of counts, let alone during a preset time period. A second conventional apparatus has a built-in rechargeable battery. This is disadvantageous since an extended time, usually four to six hours, is required to recharge the battery. Since recharging cannot occur during operation of the apparatus, should the battery require recharging during a procedure, the procedure must be stopped.

In addition, the apparatus has a hand-held probe and a remotely located control unit. The probe was merely used for detecting emitted radiation from the patient's body and transmitting electric signals representing the detected radiation to the control unit for processing. The control unit has the controls for controlling various functions including taking counts, setting the time period for taking timed counts, and initiating the taking of counts. These controls had to be activated solely at the control unit. This is disadvantageous because to conduct the counting procedure, the operator must hold and use the hand-held radiation detection probe with one hand. With the other hand, the operator needed to reach the control unit and manipulate the controls. It is difficult to conduct both the detection and control manipulation simultaneously. Also, to do so results in difficulties in taking counts and, perhaps, inaccuracies in the counts. For example, while taking a scintillation count, the probe must be precisely positioned over a selected site for a set period of time. It is difficult to maintain that precise position while reaching to depress a count start button on the control unit. Movement of the probe during counting can create an inaccurate count. Since counting is repeated at different probe angle positions over the same site and over different body sites, the difficulties and inaccuracies can be compounded. Therefore, it is desired to have an improved radiation detection apparatus that obviates or reduces such difficulties, inaccuracies and inefficiencies.

It is known to employ switches removably mounted on a handpiece. U.S. Pat. No. 5,304,763 discloses two or more finger-operated-switches removably mounted to a hand-held electrosurgical device. The switches control the application, e.g., initiation and termination, of electrical energy provided to the device. For example, one switch controls the application of energy to energize an electrode of the device for cutting body tissue. The other switch energizes a suction portion of the device to remove cut tissue from the body.

Heretofore, hand-held radiation detection probes and their cables have had to be sterilized to be re-usable because they become contaminated during use. Sterilizing such hand-held detection devices prior to each use is expensive, time consuming and may require maintaining a larger than necessary inventory of the probes and cables. It is desired to have an apparatus that obviates the need for sterilizing hand-held devices or probes prior to their re-use. It would also be desired to have an apparatus that allows for the use of hand-operated switches mounted on the hand-held device or probe during use, but permits removal from it during sterilization of the device or probe.

SUMMARY OF THE INVENTION

It is an object of the present invention to provide an improved radiation detection apparatus that includes a hand-held radiation detection probe with at least one switch removably mounted thereon.

It is another object of the present invention to provide such a radiation detection apparatus in which the one switch has a first trigger or button that remotely enables a counter in a control unit to accumulate electrical signals representing radiation scintillation detected over a set time period, and a second button that remotely directs the control unit to ouput data regarding the counted scintillations.

It is still another object of the present invention to provide such a radiation detection apparatus that allows the operator to operate a hand-held probe, while simultaneously using the switches mounted on the probe to control a remote control unit.

It is yet another object of the present invention to provide such a radiation detection apparatus in which the control unit is battery operated to provide total mobility of the control unit.

It is a further object of the present invention to provide such a radiation detection apparatus that has a removable, rechargeable battery as its power source.

It is still a further object of the present invention to provide such an improved radiation detection apparatus that enables a hand-held radiation detection probe to be reused without prior sterilization.

It is yet a further object of the present invention to provide such a hand-held radiation detection probe with a cover to protect the probe from contamination during use, and to isolate electrically the switch from the hand-held probe.

It is still yet a further object of the present invention to provide such an improved radiation detection apparatus that is removably mounted on a movable stand.

These and other objects of the present invention are achieved by a radiation detection apparatus comprising: means for counting a scintillation count value; means for outputting a scintillation count value to a utilization device; a hand-held probe including a scintillation detector; means for connecting the probe to the count means; first means removably positioned on the probe for, in a first state, causing the count means to accumulate a scintillation count over a first period, and in a second state, causing the count means to accumulate a scintillation count over a second period, the second period being longer than the first period; and second means removably positioned on the probe for causing, upon activation, the output means to manifest an accumulated scintillation count from the count means.

The radiation detection apparatus can include means for displaying a count value of the count means. The display means responds to activation to the second state of the first means, by displaying a count value accumulated over the second period for a preset time period.

Preferably, activation of the second means is operative, only during the preset time period, to cause the output means to manifest a scintillation count accumulated during the second period from the counter means. Activation of the second means, at times other than during the preset time period, causes activation of any selected other function of the control unit.

The radiation detection apparatus can include a movable stand having a holder for releasably mounting the probe on the stand.

The present invention also includes a hand-held radiation detection probe having a flexible removable protective covering thereover to protect the probe from contamination during storage or use, and permit the probe to be re-used without prior sterilization. Preferably, the covering is a sheath.

The present invention may further include a hand-held radiation detection probe having a switch assembly removably mounted thereon. The switch assembly has at least one switch, an insulating member for electrically insulating said switch from said probe which is a saddle formed by a spaced, opposed pair of cooperative depending gripping members adapted to releasably grip said probe therebetween.

DETAILED DESCRIPTION OF THE INVENTION

Figure 1:
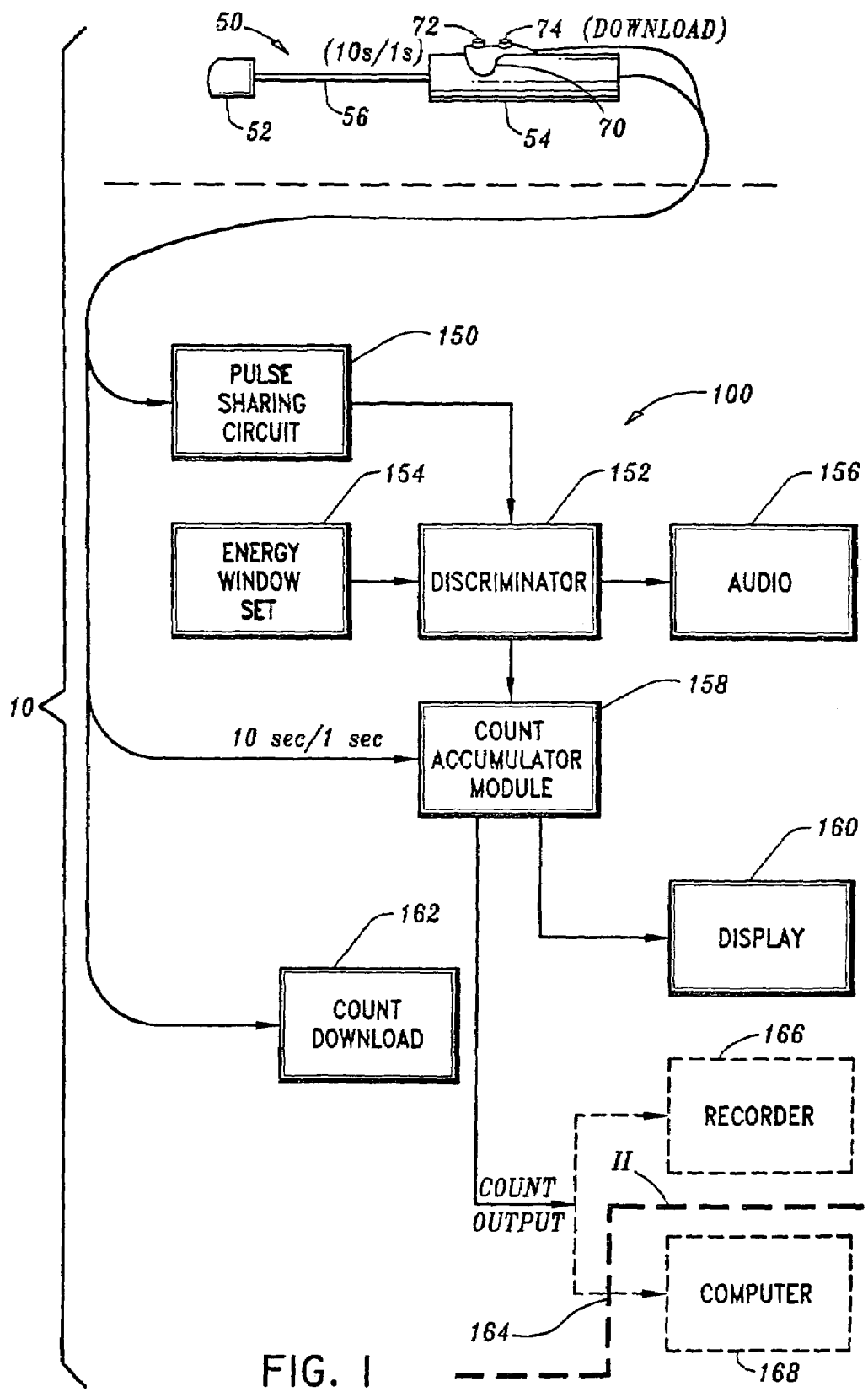
FIG. 1 is a schematic representation of the radiation detection apparatus of the present invention.

Referring to the drawings and, in particular, FIG. 1, there is a schematic of a preferred embodiment of the radiation detection apparatus of the present invention, generally represented by reference number 10. Apparatus 10 includes a hand-held radiation detection device or probe 50, and a control unit 100 connected to probe 50 by a suitable connection, such as a flexible cable 12. Probe 50 includes a radiation detector 52, a handle 54, and a shaft 56 that connects detector 52 to handle 54. Detector 52 includes a crystal, such as a cadmium telluride crystal, for detecting radiation, such as gamma protons, emitted from a radiation source in a patient's body. The radiation source is a scintillation fluid preferably containing technetium 99.

Probe 50 converts the detected scintillation radiation into electrical pulses that are amplified and transmitted through cable 12 to control unit 100. Removably mounted to probe 50 is a switch assembly 70. Assembly 70 preferably has two switches 72, 74. Switches 72, 74 are preferably push button switches.

Activation of switch 72 enables a count accumulator module 158, described below, to accumulate a scintillation count over a preset time period, such as ten seconds. Otherwise, scintillation counts are accumulated over succeeding one second periods. The scintillation pulses detected by probe 50 pass from the probe through cable 12 to a pulse shaping circuit 150 where the scintillation pulses are shaped. The shaped pulses are fed to a discriminator 152 which passes pulses that fall within an energy window that has been preset for technetium 99 by an energy window set 154. The pulses passed by discriminator 152 are fed to an audio unit 156 where they are broadcast to aid the probe operator in positioning probe 50.

Pulses from discriminator 152 are also fed to a counter, for example a count accumulator module 158. Module 158 counts the scintillation pulses and averages them, in the normal operational mode, over succeeding one second periods, or over a preset period, such as a ten second period, if selected by the probe operator's activation of switch 72 instead of pressing button 108 on control unit 100. The accumulated and averaged count value is passed from count accumulator module 158 to a display unit 160 that displays the averaged count value for each one second period, or for the preset 10 second period.

Upon activation of switch 74 on probe 50, the accumulated and averaged count value is also passed from module 158 through a download control 162 and output to a terminal, here shown as output terminal 164. Output terminal 164 can be connected to a utilization device, such as a recorder 166. Output terminal 164 may also be connected, directly or remotely, to a computer 168. Computer 168 can be, for example, a personal computer, laptop, or other computing device, for storage and manipulation of the output data.

The electronic signals sent by control unit 100 to computer 168 represents the ten second count frozen and shown on display 160. Signals received by computer 168 will be received by its software which will record the signals, for example, to keep patient records of how control unit 100 was used (settings, duration, etc.). The software can be tailored to individual preferences or to established clinical protocols. However, control unit 100 and probe 50 must be kept electrically isolated from computer 168, and the computer must not be able to control, program or otherwise affect the performance of the control unit or the probe. Thus, a unidirectional (control unit 100 to computer 168) isolated interface, e.g. optical coupler (represented by the heavy dashed line II) is employed should the computer be connected to output terminal 164.

After a patient has been injected with a radiation emitting substance, for example, a scintillation liquid containing technetium 99, hand-held probe 50 is held stationary in position over a radiation detection site on the patient's body. A count is taken of the scintillation detected at that site for a given time period. This process is repeated at one or more different sites, or for different angular positions of the probe on the same site, and a comparison is made of the counts obtained at each site. With switch 72 in a deactivated position, scintillations are detected or sampled over a series of first count sampling periods. Each sample period is, for example, preferably of one second duration. The signals or pulses transmitted from probe 50 during each one second period cause count accumulator module 158 to accumulate a scintillation count that is an average of the scintillation pulses over the one second period.

Control unit 100 is set such that activation of switch 72 initiates a ten second count sampling period, followed by a three second freeze period of the average count taken for the ten second period. During the ten second sampling period, module 158 accumulates and averages the scintillation counts taken over the ten second period. The average count is displayed on display 160 for the three second freeze period. During the sampling period, a sampling light (not shown) on control unit 100 will flash. At the end of the sampling period, the sampling light goes off and a single audible beep is emitted. If, during the three second freeze period, switch 74 is activated by the operator, the frozen count is downloaded from module 158 to output terminal 164 which sends the frozen count to a utilization device.

When switch 74 is activated during the three second period, two audible beeps are emitted. If switch 74 is not activated during the freeze period, no downloading of the frozen count occurs. Switch 74 can be activated during or at the end of any one second count sampling period or, as stated above, during the three second freeze period. Thus, activation of switch 74 downloads the ten second count value to output terminal 164, and an audible signal indicates that the download has occurred. If switch 74 is not activated during the three second freeze period, module 158 returns to its normal mode of accumulating and averaging sampled counts per second and displaying the counts per second on display 160.

Control unit 100 is powered by a removable, rechargeable battery. The preferred battery is a lead-acid rechargeable battery capable of four hours of continuous operation. When a predetermined set period of time of power battery life remains, such as, for example, fifteen minutes, a warning indicator, such as a light, will flash or indicate the commencement of that set period.

Accordingly, the user can simply insert a second battery in the control unit 100 to operate the control unit, and the first battery can simply be recharged when desired.

Figure 2:
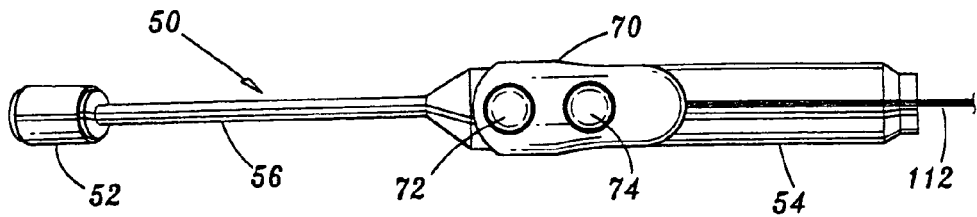
FIG. 2 is a top plan view, with portions broken away, of a preferred embodiment of the probe shown in FIG. 1.

As shown in FIG. 2, switch assembly 70 is removably mounted on handle 54 of probe 50. Switch assembly 70 preferably has two finger-operated push button switches 72, 74.

Figure 3:
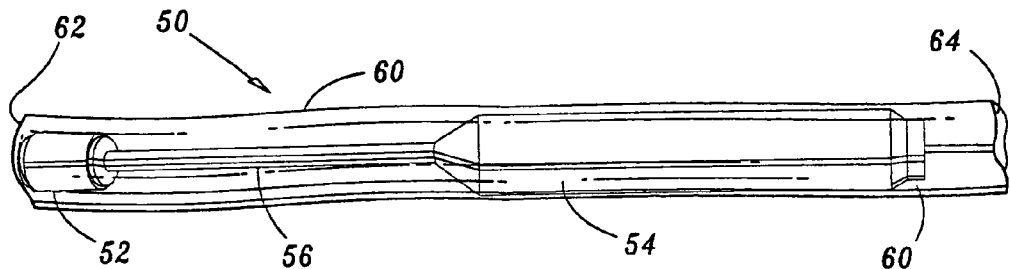
FIG. 3 is a top plan view, with portions broken away, of the probe shown in FIG. 2 without a switch mounted thereon and covered by a sheath.

Referring to FIG. 3, probe 50 may have a removable protective cover 60 placed thereover. The protective cover 60 preferably is a sheath that substantially fully encompasses probe 50 to protect it from being soiled or contaminated during storage and use. Sheath 60 permits probe 50 to be re-used without prior sterilization. Sheath 60 has a closed end 62 that covers detector 52, and an opposite open end 64 that can be at any desired location beyond handle 54. Preferably, sheath 60 is long enough to the entire length of cable 12, as shown in FIG. 2.

Figure 4:
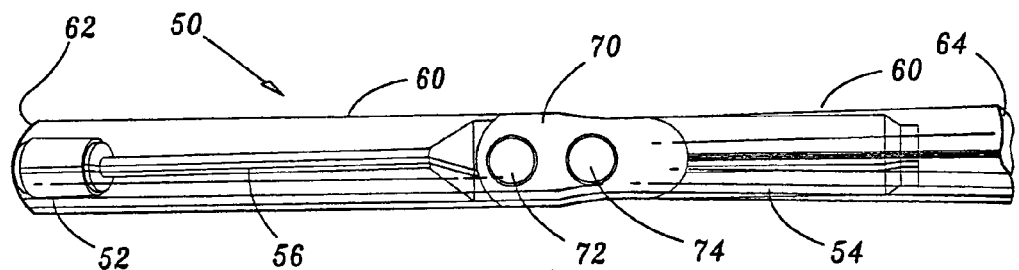
FIG. 4 is a top plan view, with portions broken away, of the probe shown in FIG. 2 covered by a sheath and having a switch assembly mounted thereon.

Sheath 60 can have any suitable size, shape and configuration. Thus, it can fit loosely, tightly or form-fitted or even shrunk onto probe 50. As shown in FIG. 4, sheath 60 preferably fits sufficiently tightly onto probe 50, especially about detector 52, to minimize interference with its function. Sheath 60 preferably also fits tightly about the portion of handle 54 onto which switch assembly 70 is to be mounted, to enable the switch assembly to remain tightly and securely mounted onto the handle. Sheath 60 can be made of any suitable material or materials, and can be single or multiple layered. Preferably, sheath 60 is made from a flexible film or sheet. The preferred material for sheath 60 is a single layer of polyurethane.

Figure 5:
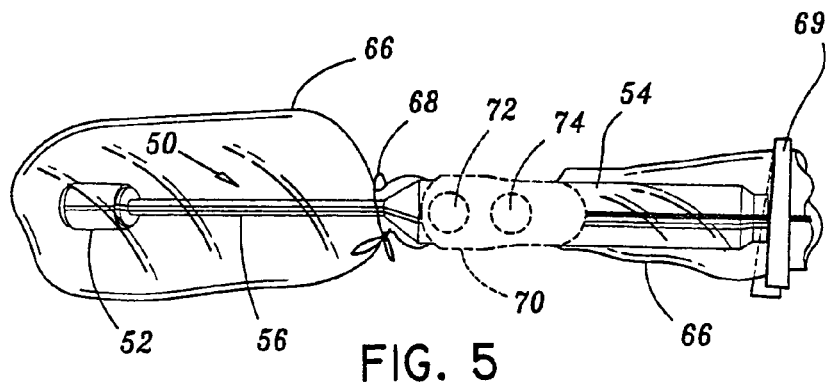
FIG. 5 is a top plan view, with portions broken away, of the probe shown in FIG. 2 covered by a drape and with a switch assembly shown optionally mounted thereon.

Although sheath 60 is the preferred cover, any suitable cover can be employed that permits switch assembly 70 to be effectively mounted onto probe 50. The sheath 60 is removable and preferably disposable and easily replaceable. Thus, as shown in FIG. 5, a drape 66 of flexible film can be placed over and secured to probe 50. As shown in FIG. 5, a continuous portion of drape 66 can be placed over detector 52, tied around shaft 56 by a tie 68, and gathered and secured about handle 54 or about cable 12 (not shown) by any suitable member, such as by a clip 69. Switch assembly 70 (dashed line) can be mounted on probe 50 awhile the switch assembly is covered by drape 66.

Figure 6:
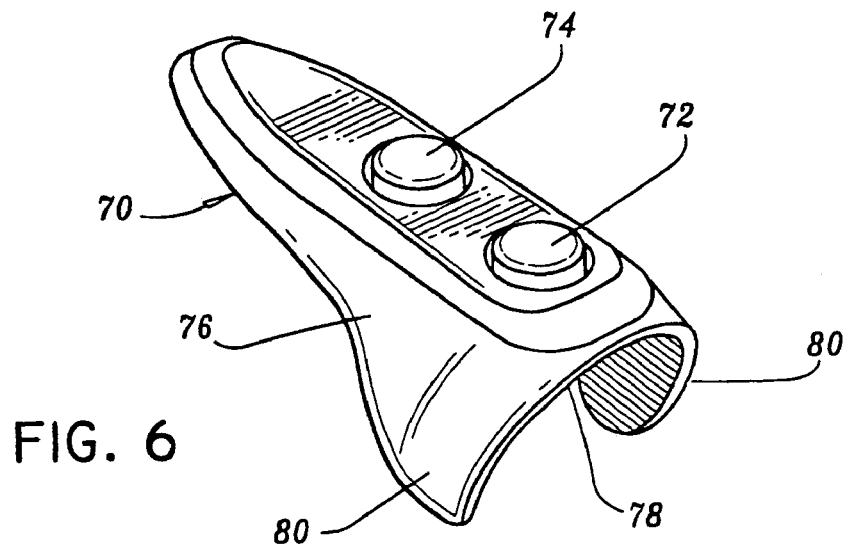
FIG. 6 is a perspective view of the removable switch assembly that is mounted on the probe shown in FIG. 2.

Referring to FIG. 6, switch assembly 70 preferably has a saddle 76 formed by a curved undersurface 78 and a pair of spaced opposed cooperative depending gripping members 80 that are adapted to releasably grip probe 50 (not shown) between them. Gripping members 80 are arcuately shaped and sized to fit tightly about handle 54 of probe 50. Gripping members 80 are rigid enough to hold probe 50 between them, but resilient enough to allow the switch assembly 70 to be removed from the probe.

Figure 7:
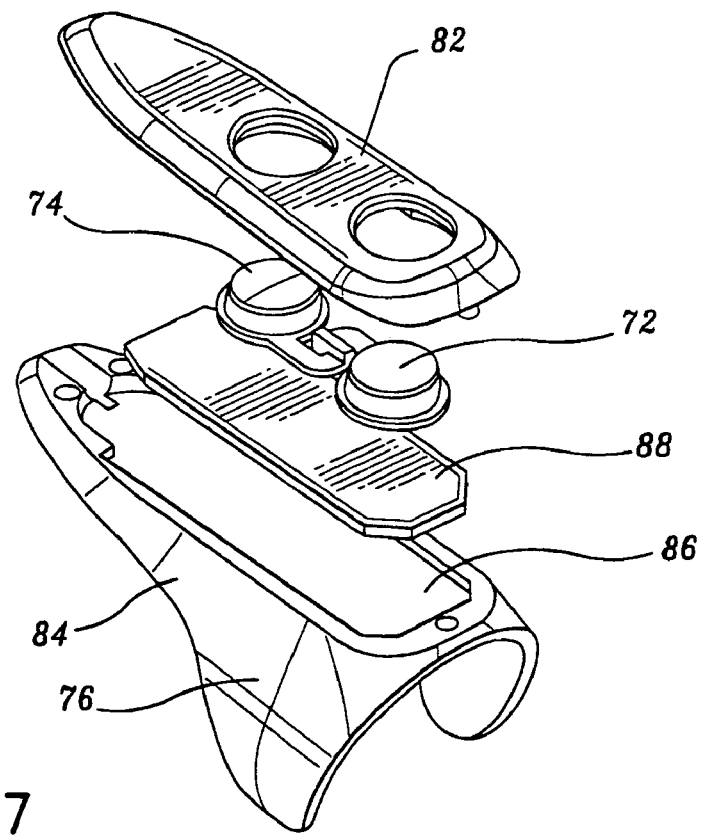
FIG. 7 is an exploded perspective view of the switch assembly shown in FIG. 6.

As shown in FIG. 7, the preferred switch assembly 70 also has a cover 82, button switches 72, 74, a carrier in the form of a mounting member 84 having saddle 76, a recessed panel 86, and an insulating member 88 that fits into recessed panel 86 and insulates the switches and any electrical wiring and connections (not shown) from probe 50 (not shown). In a preferred embodiment, there are two switches 72, 74. However, it is possible that these switches may be combined into a single switch or that a third or more switches may be added to control remotely other functions of control unit 100.

Figure 8:
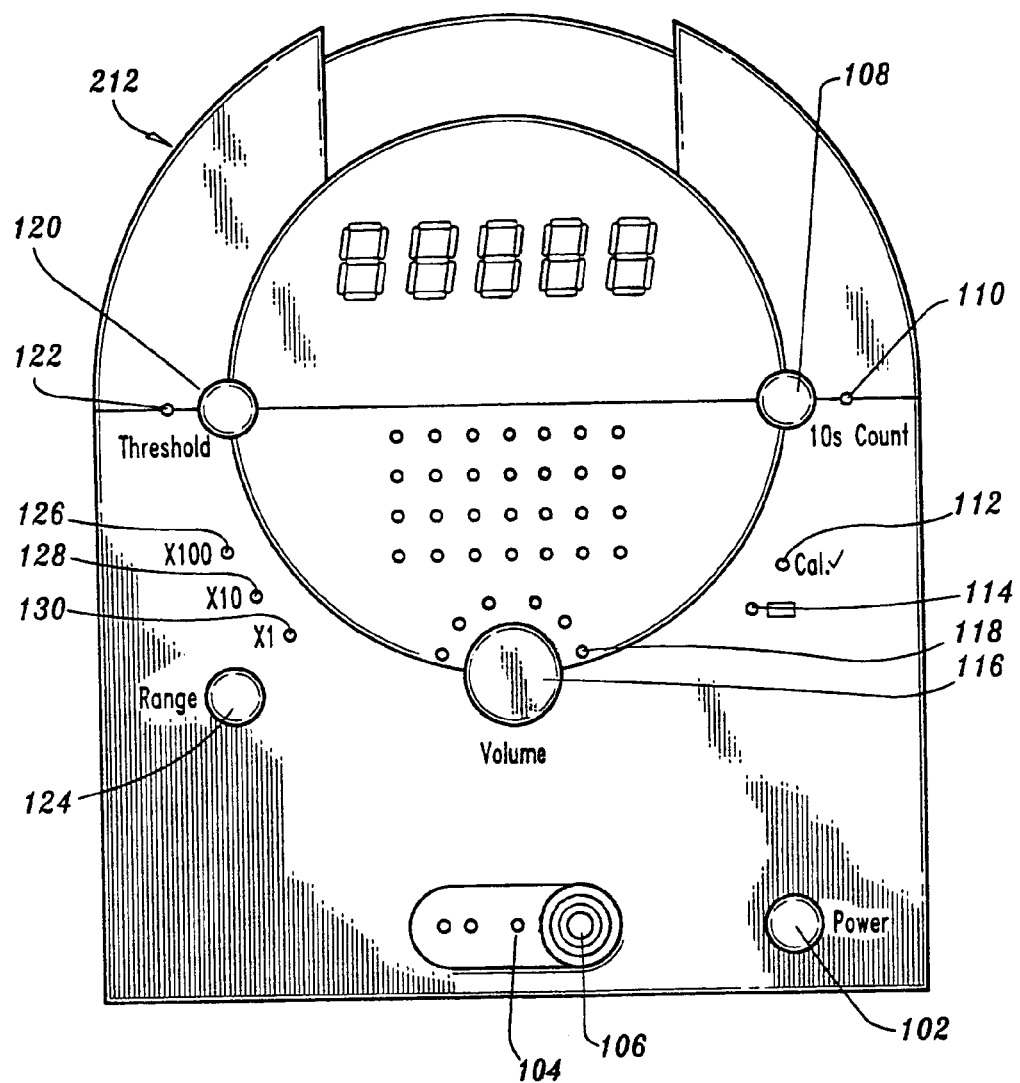
FIG. 8 is a front view of the housing of the control unit of the present invention.

Referring to FIG. 8, housing 212 of control unit 100 has a power button 102, a plurality of holes 104, preferably three, for operatively receiving a three prong plug of cable 12, a receiver 106 for operatively receiving a plug connected to probe 50, and a digital display 130. Housing 212 also has a button 108, which is preferably a push button, that initiates the ten second count time period, a light 110 that lights during the ten second period, a calibration indicator 112, and a battery charge indicator light 114. Housing 212 also has a volume control knob 116, a plurality of volume indicators 118, preferably light indicators, a knob to deactivate an internal threshold and window pre-set for technetium 99 to permit setting a wider window, a light indicator 122 for the internal threshold, and an audio range knob 124 to change the audio range from among the three values indicated by lights 126, 128 and 130. Referring to FIGS. 6 and 8, when switch 72 of switch assembly 70 is activated, button 108 is activated and, thus, light 110 is activated. When switch 74 is activated to download or record a count, an audible signal is provided.

Figures 9, 10:
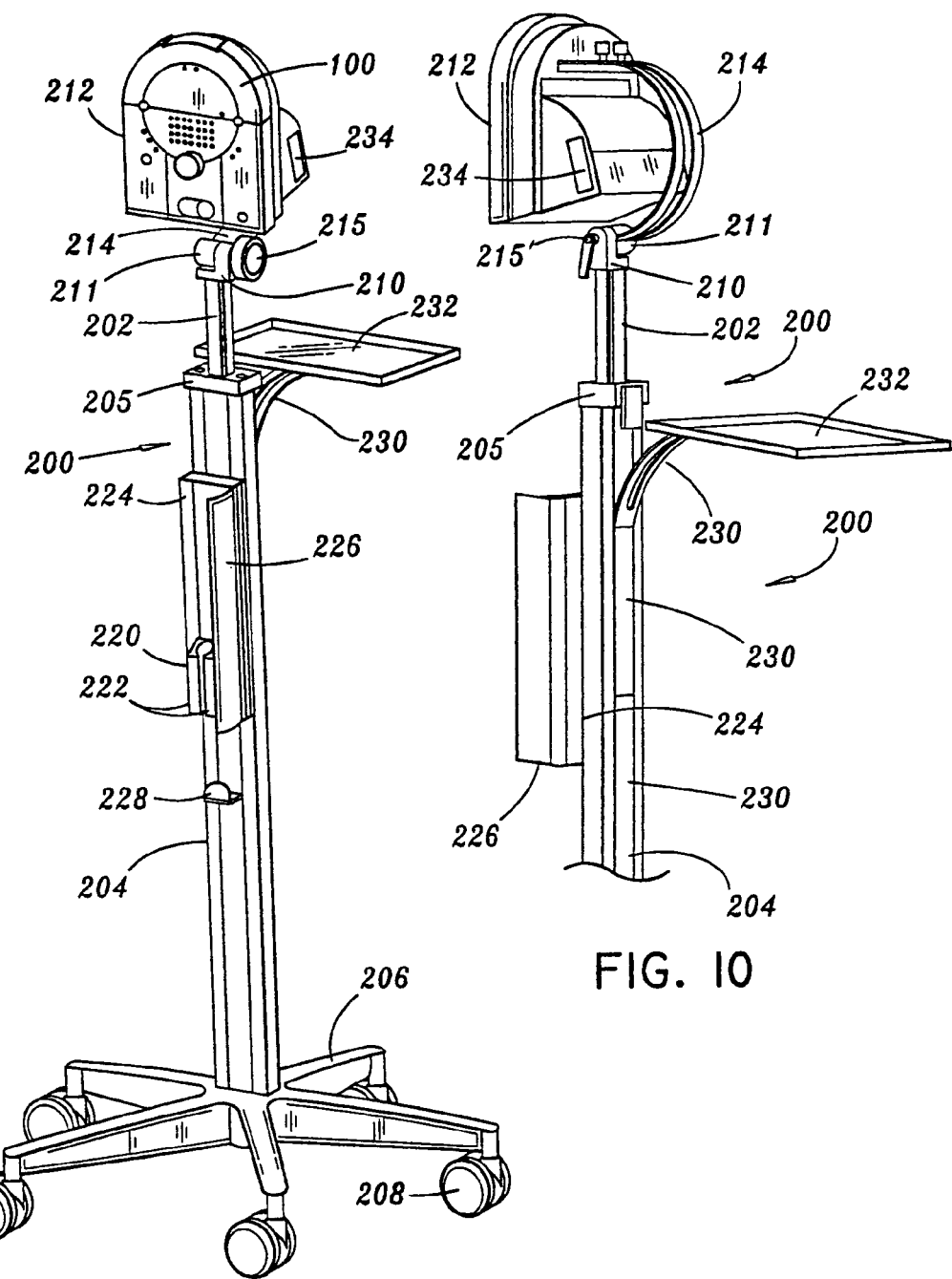
FIG. 9 is a front perspective view of a movable stand for mounting the control unit of the radiation detection apparatus of FIG. 1.
FIG. 10 is a rear perspective view, with portions broken away, of the control unit and stand shown in FIG. 9.

FIGS. 9 and 10 show a movable stand 200 suitable for use with radiation detection apparatus 10 of the present invention. Stand 200 has an upper vertical shaft 202 telescopically seated with a lower vertical shaft 204. Shaft 204 is mounted at its bottom end onto the hub of a plurality of radially outwardly extending legs 206 supported on rotatable wheels 208. Shaft 202 is held at a desired height by an adjustable restrainer 205 on the top end of shaft 204. The upper end of shaft 202 has an adjustable fastener 210 mounted thereon. Fastener 210 has a horizontal shaft (not shown) onto which the lower end 211 of a bracket 214 is rotatably mounted. A housing 212 of control unit 100 is secured to bracket 214. Bracket 214 and housing 212 can be tilted up and down to a desired angle about the shaft of fastener 210 and held at the desired angle by tightening threaded bolt 215.

Lower shaft 204 preferably has a pair of holders 220 mounted thereon. Each holder 220 has a pair of spaced, vertically disposed opposed holding members 222 adapted, e.g. shaped, to receive and releasably hold probe 50. Each holder 220 is positioned within a protective box 224 having a cover 226. Lower shaft 204 preferably has a support 228 for supporting cable 12 for probe 50. Onto the rear of lower shaft 204, there is preferably fixedly mounted the lower end of an elongated bracket 230. Bracket 230 has a platform 232 welded or otherwise fixed thereto. Platform 232 preferably is for supporting an auxiliary component such as a computer (not shown). The side of housing 212 has an angularly disposed rectangular cavity at 234 for holding and accessing the replaceable rechargeable battery (not shown) to supply power to control unit 100.

The present invention having been thus described with particular reference to the preferred forms thereof, it will be obvious that various changes and modifications may be made therein without departing from the spirit and scope of the present invention as defined in the appended claims.

What is claimed is:

1. A radiation detection apparatus comprising:
   a hand-held probe having a scintillation detector;
   a counter operably connected to said hand-held probe for counting first and second scintillation count values;
   a control device for outputting at least one of the scintillation count values to a utilization device;
   a display operably connected to said counter for displaying at least one of the scintillation count values; and
   a switch assembly adapted to be removably mounted to said hand-held probe and including first and second switches, said first switch in a first state remotely causing said counter to accumulate said first scintillation count value and in a second state remotely causing said counter to accumulate said second scintillation count value, said second switch in a first state remotely causing said first scintillation count value to be communicated to said utilization device and in a second state remotely causing said second scintillation count value to be communicated to said display.

2. The radiation detection apparatus of claim 1, wherein said first scintillation count value is accumulated over a first time period.

3. The radiation detection apparatus of claim 2, wherein said second scintillation count value is accumulated over a second time period.

4. The radiation detection apparatus of claim 3, wherein said first time period is greater than said second time period.

5. The radiation detection apparatus of claim 1, wherein said switch assembly further includes a carrier formed from a mounting member having a saddle, said saddle including a pair of cooperative depending gripping members adapted for releasably mounting said switch assembly to said hand-held probe.

6. The radiation detection apparatus of claim 1, wherein said display displays said first scintillation count value for a preset time period.

7. The radiation detection apparatus of claim 6, wherein said second switch is in said first state during said preset time period and causes said control device to output said first scintillation count value accumulated during a second time period from said counter.

8. The radiation detection apparatus of claim 6, wherein said preset time period is about three seconds.

9. The radiation detection apparatus of claim 1, wherein said control device downloads to said utilization device through an electrically isolating interface that precludes reverse signal transfer from said utilization device.

* * * * *